United States Patent [19]

Cassar et al.

[11] 4,118,589

[45] Oct. 3, 1978

[54] PROCESS FOR PREPARING OXALIC ACID AND ESTERS OF SAME

[75] Inventors: Luigi Cassar, Novara; Andrea Gardano, Trino Vercellese (Vercelli), both of Italy

[73] Assignee: Montedison S.p.A., Milan, Italy

[21] Appl. No.: 649,235

[22] Filed: Jan. 15, 1976

[30] Foreign Application Priority Data

Jan. 17, 1975 [IT] Italy .................... 19339 A/75

[51] Int. Cl.² .................... C07C 51/00; C07C 55/06; C07C 69/36
[52] U.S. Cl. .................... 560/204; 562/519
[58] Field of Search .................... 260/485 R, 538; 560/204

[56] References Cited

U.S. PATENT DOCUMENTS

| | | | |
|---|---|---|---|
| 3,393,136 | 7/1968 | Fenton et al. | 260/485 R |
| 3,994,960 | 11/1976 | Yamazaki et al. | 260/485 R |
| 4,005,128 | 1/1977 | Zehner | 560/204 |
| 4,005,129 | 1/1977 | Zehner | 560/204 |
| 4,005,131 | 1/1977 | Zehner | 560/204 |

FOREIGN PATENT DOCUMENTS 2,213,435 10/1973 Fed. Rep. of Germany ...... 260/485 R

OTHER PUBLICATIONS

Fenton, et al., J. Org. Chem. 39, No. 5, pp. 701–704 (1974).

*Primary Examiner*—Jane S. Myers
*Attorney, Agent, or Firm*—Morgan, Finnegan, Pine, Foley & Lee

[57] ABSTRACT

The present invention relates to a process for preparing oxalic acid and esters of oxalic acid. More particularly, this invention relates to a catalytic process for preparing oxalic acid and esters of same by the oxidative reaction, in a liquid phase, of carbon monoxide and water or alcohols with oxygen in the presence of redox systems.

The catalyst systems used in accordance with this invention comprises a redox catalyst consisting essentially of a salt of Pd (II) and salts of a metal more electropositive than Pd having at least two oxidation states and, optionally, salts of alkaline metals, and co-catalytic amounts of at least one base having the formula $R_3N$ in which the groups R which may be like or unlike and are selected from the group consisting of hydrogen and alkyl radicals having from 1 to 10 carbon atoms.

9 Claims, No Drawings

PROCESS FOR PREPARING OXALIC ACID AND ESTERS OF SAME

BACKGROUND OF INVENTION

Oxalic acid and esters are important compounds having a known and wide application field of considerable commercial interest. Oxalic acid may be used in the textile industry as the auxiliary agent for "stripping" in the dyeing of wool, as a bleaching agent for natural fibers, as a pickling agent for metal surfaces, especially of copper; in the industry it can be utilized as a dehydrogenating agent in condensation reactions, etc. Finally, the esters are known solvents, such as, for instance, diethylester for cellulose.

It is known how to prepare oxalic esters by the oxidative reaction of carbon monoxide and monobasic alcohols with oxygen and also quinones, preferably in a substantially anhydrous medium due to the presence of dehydrating matters, and catalyzed by redox systems usually consisting of a finely subdivided metal or of soluble salts or complexes (citrates, kelates) of a noble metal of the Pt group, such as Pd, U, Os, or of a salt and/or a complex of another metal more electropositive than the preceding ones, such as Fe, Co, Ni, Cu, Mn, etc., such as chlorides, acetates, etc., having several oxidative states. Reaction is preferably conducted in the presence of a co-catalysts and/or complexing agents consisting of soluble salts of alkaline metals (LiCl, KCl, etc.). Processes of the aforedescribed type are disclosed in U.S. Pat. No. 3,393,136 and German Patent Publication No. 2,213,435.

Processes of the aforedescribed type, however, due to the contemporaneous occurrance of secondary reactions leading to the forming of carbonates, $CO_2$, esters (acetates, formates, etc.), cannot be considered as thoroughly satisfactory from a commercial viewpoint owing to the low yields and the relative expensive separation, purification, etc. operations.

On the other hand, other processes known in the art for producing oxalic esters such as, for example, those based on the dehydrogenation of sodium formate successively transformed into calcium oxalate acidified etc., or an oxidation of propylene with $NHO_3$ catalyzed by Fe, Cr, etc., do not yield better results, though involving considerable technological and operative difficulties that render them less profitable especially for commercial scale productions.

Thus, it is an object of the present invention to provide a simple and economic process for preparing oxalic acid and alkyl esters of same, free from the drawbacks of the prior art and, in particular, capable of providing high yields and purity of the products and representing an actual progress with respect to the prior art.

GENERAL DESCRIPTION OF THE INVENTION

This and further objects too, that will more clearly result to those skilled in the art from the following description, are achieved, according to this invention, through a process for preparing oxalic acid and alkyl esters of same, which is based on the oxidation, in the liquid phase, of CO and $H_2O$ or mono-functional alkyl alcohols with oxygen and/or a gas containing it, in the presence of a catalytic system of the redox type based on salts of Pd (II), on salts of a metal more electropositive than Pd having at least two oxidative states and, optionally, on salts of alkaline metals, and characterized in that it is conducted in the presence of co-catalytic amounts of at least a $R_3N$ base in which the R groups, either like or unlike one another, are selected from amongst H and the alkyl radicals having 1 to 10 carbon atoms.

This invention is to be considered so much the more surprising in that it represents a remarkable overcoming of a prejudice existing in the art, which is substantially explicit in regarding as harmful the presence of bases in the oxidative carboxylation on which the considered reaction is based; a prejudice that, obviously, would have dissuaded those skilled in the art from carrying out further researches in this sense. Oxalic acid or esters are therefore obtained by the reaction of carbon monoxide and oxygen in an aqueous or alcoholic phase in the presence of the catalytic system described hereinbefore.

Salts which are soluble in the reaction medium such as halides, sulphates, nitrates, etc., preferably chloride, may be employed as salts of Pd (II), but it is also possible to use Pd (zero-valent).

Suitable salts of alkaline metals are alkali metal halides such as LiCl, NaCl, KCl, etc., and, analogously, the usual metals more electropositive than Pd and having at least two oxidative states are Co, Fe, Ni, preferably Cu, in the form of soluble salts such as the halides, etc.

As to the $R_3N$ base, it is made up of primary, secondary, tertiary amines or mixtures of same, in which alkyl radical R contains up to 10 carbon atoms, but preferably it is ammonia with R = H.

Suitable alcohols are methanol and ethanol.

The palladium salt concentration in the reaction mass is comprised between 0.0001 and 1.0 moles/liter of the reaction mass.

The concentration of the metal more electropositive than palladium ranges from 0.01 to 1.0 moles/liter of the reaction mass.

The molar ratio between the metal more electropositive than palladium and $R_3N$ base shall be comprised between 1:1 and 1:5. Amine can be introduced into the catalytic system in the form of complexes with the metal more electropositive than Pd, preferably with Cu.

The employable reaction temperature ranges from 20° to about 100° C., preferably from 20° to about 60° C. At higher temperatures the selectivity decreases.

Reaction times may vary over a wide range, depending upon the temperature and pressure employed. The useful pressure ranges from 10 to about 150 atm. abs., the composition of the gases, CO and $O_2$, mixture being comprised in a wide range. The use of air and/or $O_2$ in admixture with inert gases is allowable.

The use of the $R_3N$ base as a co-catalyst permits the attainment of higher yields than if it were absent.

Amine concentration, however, shall be kept within the above-said range, that is discriminant for the process efficiency. In fact, in the presence of amine concentrations exceeding the above-mentioned range, the forming of the oxalate is firstly depressed, under formation of by-products such as R—NH—$COOCH_3$, until obtaining no reaction at amine concentrations higher than 5–10 molar.

The reaction product may be easily separated from the solvent and from the catalyst by distillation, etc. according to conventional techniques.

The distillation residue containing the catalyst system may be employed for further reactions without regeneration, provided small amounts of amine are previously added. Due to the bland operative conditions, the present invention appears to be particularly advantageous.

Another advantage consists in the particular selectivity towards the desired products, made possible by the catalyst system herein described.

The following examples are given to better illustrate the present industrial invention, without being, however, a limitation thereof.

Examples 1, 2, 3, 5, 9 and 13 include also comparisons with the most pertinent art.

SPECIFIC DESCRIPTION OF INVENTION

Example 1

20 ml of methanol, 0.07 g of $PdCl_2$, 0.5 g of $CuCl_2$, 0.037 g of LiCl, 0.2 g of $NH_3$ were introduced into a stainless steel, 100 ml autoclave.

100 atm. of CO and 20 atm. of $O_2$ were then added, the temperature was brought to 60° C. and kept such for 4 hours.

The reaction raw product was distilled, thus obtaining 2.3 g of methyl oxalate (boiling point = 65°–67° C./12 mm Hg; melting point = 53° C.). Yield on reacted CO : 90%.

Under the same conditions, in the absence of $NH_3$, 0.23 g of methyl oxalate was obtained.

Under the same conditions, but in the presence of 0.7 g of $NH_3$ ($NH_3$/Cu = 11), 0.4 g of methyl oxalate was obtained.

Example 2

The same reaction mixture of the preceding example was reacted, under the same conditions of Example 1, at 40° C. for 4 hours, 1.4 g of methyl oxalate being thus obtained. Yield on reacted CO : 95%.

Under the same conditions, in the absence of $NH_3$, 0.09 g of methyl oxalate were obtained.

Example 3

Operating under the same conditions of Example 1, the same reaction mixture was reacted at 20° C. for 4 hours, obtaining 1.0 g of methyl oxalate. Yield on reacted CO : 95%.

In the absence of $NH_3$, only traces of methyl oxalate (<0.005 g) were obtained.

Example 4

The same reaction mixture was reacted, under the same conditions of Example 1, in a one-liter autoclave, complete with a glass phial, at 20° C. for 23 hours, obtaining 3.4 g of methyl oxalate. Yield on reacted CO : 95%.

Example 5

20 ml of methanol, 0.07 g of $PdCl_2$, 0.5 g of $CuCl_2$, 0.037 g of LiCl and 0.5 g of 1-hexylamine were introduced into a 100 ml autoclave. Successively, 100 atm. of CO and 20 atm. of oxygen were charged thereinto, whereupon the temperature was brought to 60° C. and kept at such value for 4 hours.

The reaction raw product was distilled, thus obtaining 0.83 g of methyl oxalate. Yield on reacted CO : 85%.

Under the same conditions, in the absence of hexylamine, 0.23 g of methyl oxalate, was obtained.

Example 6

By operating under the same conditions as in Example 4, but employing triethylamine instead of 1-hexylamine, 0.88 g of methyl oxalate was obtained. Yield on reacted CO : 85%.

Example 7

20 ml of methanol, 0.07 of $PdCl_2$, 0.5 g of $CuCl_2$, 0.037 g of LiCl and 0.2 g of $NH_3$ were introduced into a 100 ml autoclave.

After having charged 50 atm. of CO and 10 atm. of oxygen, the temperature was brought to 40° C. and kept such for 4 hours. 0.70 g of methyl oxalate were obtained by distillation. Yield on reacted CO : 90%.

Example 8

20 ml of methanol, 0.07 g of $PdCl_2$, 0.5 g of $CuCl_2$, 0.037 g of LiCl and 0.2 g of $NH_3$ were introduced into a 100 ml autoclave.

Successively, 100 atm. of CO were charged, the temperature was brought to 40° C. and 15 atm. of $O_2$, in amounts of 5 atm. at a time, were fed in 4 hours. 1.34 g of methyl oxalate were obtained by distillation. Yield on reacted CO : 90%.

EXAMPLE 9

20 ml of ethanol, 0.07 g of $PdCl_2$, 0.5 g of $CuCl_2$, 0.037 g of LiCl and 0.2 g of $NH_3$ were introduced into a 100 ml autoclave.

After having raised the temperature to 40° C., 100 atm. of CO and 20 atm. of $O_2$ were introduced into the autoclave. After 4 hours, 1.05 g of ethyl oxalate were obtained by distillation of the reaction mixture. Yield on reacted CO : 85%.

In the absence of $NH_3$ no ethyl oxalate could be obtained.

Example 10

20 ml of methanol, 0.07 g of $PdCl_2$, 0.5 g of $CuCl_2$ and 0.2 g of $NH_3$ were introduced into a 1 l autoclave equipped with a glass vial.

Successively, 100 atm. of CO and 20 atm. of oxygen were charged, the temperature was brought to 40° C. and kept at such value for 4 hours.

The reaction raw product was distilled, yielding 2.47 g of methyl oxalate. Yield on reacted CO : 85%.

Example 11

20 ml of methanol, 0.07 g of $PdCl_2$, 0.037 g of LiCl and 0.6 g of complex $CuCl_2(NH_3)_3$ were introduced into a 100 ml autoclave. 100 atm. of CO and 20 atm. of $O_2$ were then added, the temperature was brought to 40° C. and kept such for 4 hours. The reaction raw product was distilled, thus obtaining 2.66 g of methyl oxalate. Yield on reacted CO : 90%.

Example 12

By operating under the same conditions of Example 11, but using, instead of $PdCl_2$, 1.0 g of Pd on carbon at 5%, 1.78 g of methyl oxalate were obtained. Yield on reacted CO : 90%.

Example 13

20 ml of methanol, 0.07 g of $PdCl_2$, 0.037 g of LiCl, 0.5 g of $CuCl_2$ and 0.15 g of sodium salt of ethylene diamine tetraacetic acid were introduced into a 100 ml autoclave. Then, after having charged 100 atm. of CO and 20 atm. of oxygen, the temperature was brought to 40° C. No gas oxide absorption took place. The specimen thus obtained was treated in the usual way and no traces of methyl oxalate could be noticed.

What we claim is:

1. A process for the preparation of oxalic acid and alkyl esters of oxalic acid by the oxidation, in the liquid phase, of carbon monoxide and a liquid selected from the group consisting of water and monofunctional alkyl alcohols with a gas selected from the group consisting of oxygen and oxygen-containing gases, in the presence of a catalyst system of the redox type consisting essentially of palladium salts of Pd (II) or of metallic Pd (zero valent) and of soluble salts of a metal more electropositive than palladium selected from the group consisting of Cu, Co, Fe and Ni, having at least two oxidation states, being further characterized in that the reaction is conducted at a temperature ranging from 20° to about 100° C. and a pressure ranging from 10 to about 150 atm. abs. in the presence of an effective amount of a co-catalyst consisting essentially of ammonia, the concentration of the palladium salt being between 0.0001 mole per liter and 1 mole per liter, the concentration of the salt of the metal more electropositive than palladium being between 0.01 and 1 mole per liter and the molar ratios of the salt of the metal more electropositive than palladium to ammonia ranging from 1:1 to 1:5.

2. A process according to claim 1 wherein the salt of Pd (II) is selected from the group consisting of the halides, nitrates and sulphates of Pd (II).

3. A process according to claim 1 characterized in that the catalyst system contains a salt of an alkaline metal.

4. A process according to claim 3 wherein the salt of an alkaline metal is an alkali metal halide.

5. A process according to claim 1 characterized in that the catalyst system is made up of $PdCl_2$, $CuCl_2$ and $NH_3$.

6. A process according to claim 1 characterized in that the ammonia is introduced in the form of a complex with the metal more electropositive than Pd.

7. A process according to claim 6 wherein the ammonia is introduced as a complex with Cu.

8. A process according to claim 1 characterized in that it is conducted at a temperature ranging from 20° to about 60° C.

9. A process according to claim 1 characterized in that metallic Pd is used in the catalyst system.

* * * * *